(12) United States Patent
Hillhouse et al.

(10) Patent No.: US 6,563,005 B1
(45) Date of Patent: May 13, 2003

(54) PREPARATION OF MONO- AND DI-ARYLPHOSPHINES

(75) Inventors: John Henry Hillhouse, Niagara Falls (CA); William Andrew Rickleton, deceased, late of Niagara Falls (CA), by Malcolm Stockton, legal representative

(73) Assignee: Cytec Technology Corp., Wilmington, DE (US)

( * ) Notice: Subject to any disclaimer, the term of this patent is extended or adjusted under 35 U.S.C. 154(b) by 0 days.

(21) Appl. No.: 09/856,754

(22) PCT Filed: Oct. 12, 1999

(86) PCT No.: PCT/US99/23777

§ 371 (c)(1), (2), (4) Date: Feb. 1, 2002

(87) PCT Pub. No.: WO00/32613

PCT Pub. Date: Jun. 8, 2000

(30) Foreign Application Priority Data

Dec. 3, 1998 (CA) .............................................. 2255161

(51) Int. Cl.[7] .................................................. C07F 9/50
(52) U.S. Cl. ....................................................... 568/17
(58) Field of Search ....................................... 568/8, 17

(56) References Cited

U.S. PATENT DOCUMENTS

| | | | |
|---|---|---|---|
| 2,902,517 A | * | 9/1959 | Schmerling |
| 3,060,241 A | * | 10/1962 | Rauhut et al. |
| 3,099,691 A | * | 7/1963 | Rauhut et al. .................. 44/435 |
| 3,998,887 A | | 12/1976 | Allen .................... 260/606.5 P |
| 4,008,282 A | | 2/1977 | Townsend et al. ..... 260/606.5 P |
| 4,042,609 A | | 8/1977 | Perrotti et al. ........... 260/429 R |
| 4,246,204 A | | 1/1981 | Broger ......................... 568/17 |
| 4,301,301 A | | 11/1981 | Fukui et al. .................... 568/17 |
| 4,507,503 A | | 3/1985 | Frey et al. ..................... 568/17 |
| 4,507,504 A | | 3/1985 | Lee et al. ...................... 568/17 |
| 4,514,575 A | | 4/1985 | Lee et al. ...................... 568/17 |
| 4,618,720 A | | 10/1986 | Bay et al. ...................... 568/17 |
| 4,668,823 A | | 5/1987 | Murray .......................... 568/17 |
| 4,758,315 A | | 7/1988 | Folest et al. ................... 204/59 |
| 5,041,676 A | | 8/1991 | Hofmann ........................ 568/8 |
| 5,231,202 A | | 7/1993 | Hayashi et al. ................ 556/21 |
| 5,399,771 A | | 3/1995 | Cai et al. ....................... 568/17 |
| 5,510,503 A | | 4/1996 | Laue et al. ..................... 556/21 |
| 5,527,967 A | | 6/1996 | Millauer ........................ 568/17 |
| 5,530,162 A | | 6/1996 | Rothwell et al. ............... 568/8 |
| 5,550,295 A | | 8/1996 | Hillhouse ...................... 568/14 |
| 5,621,128 A | | 4/1997 | Jendralla ....................... 556/18 |
| 5,621,129 A | | 4/1997 | Hayashi et al. ................ 556/21 |
| 5,648,549 A | * | 7/1997 | Kleiner .......................... 568/17 |
| 5,693,868 A | | 12/1997 | Sayo et al. ..................... 568/8 |
| 5,710,338 A | | 1/1998 | Unruh et al. ................... 568/16 |
| 5,728,886 A | | 3/1998 | Naumann et al. .............. 568/17 |
| 6,084,133 A | * | 7/2000 | Kawashima ................... 568/17 |

FOREIGN PATENT DOCUMENTS

EP            0732336 A       9/1996    ............ C07F/9/50

OTHER PUBLICATIONS

CA:112:179474 abs of NL 8800770 Oct. 1989.*
Oliver Herd, Antonella Hebler, Klaus P. Langhans and Othmar Stelzer, "Wasserlösliche Phosphane II," Journal of Organometallic Chemistry, vol. 475, pp. 99–111, (1994).
Oliver Herd, Antonell Hebler, Martin Hingst, Michael Tepper, Othmar Stelzer, "Palladium–catalyzed P–C cross coupling reactions between primary or secondary phosphines and functional aryliodides—a novel synthetic route to water soluble phosphines," Journal of Organometallic Chemistry, vol. 522, pp. 69–76, (1996).
Scott R. Gilbertson and Gale W. Starkey, "Palladium–CatalyzedSynthesis of Phosphine–Containing Amino Acids," Journal of Organic Chemistry, pp. 2922–2923, (1996).
Wolfgang A. Herrmann, Christoph Brossmer, Karl Öfele, Claus–Peter Reisinger, Thomas Priermeier, Matthias Beller, and Hartmut Fischer, "Palladacycles as Structurally Defined Catalysts for the Heck Olefination of Chloro– and Bromoarenes,"Angew. Chem. Int. Ed. Engi., vol. 34, No. 17, pp. 1844–1848, (1995).

* cited by examiner

*Primary Examiner*—Jean F. Vollano
(74) *Attorney, Agent, or Firm*—Valerie T. Didamo; Claire M. Schultz; James A. Jubinsky

(57) ABSTRACT

Mono- and di-arylphosphines are prepared by reacting an aryl compound that has a leaving group attached to a carbon atom of the aromatic ring with phosphine in the presence of a Group VIII metal catalyst.

7 Claims, No Drawings

PREPARATION OF MONO- AND DI-ARYLPHOSPHINES

This application is a 371 of PCT/US99/23777, filed Oct. 12, 1999, now WO 00/32613.

BACKGROUND OF THE INVENTION

There are known processes to prepare arylphosphines by reacting, for example, phosphorus trichloride with a Grignard reagent or with an organolithium compound, followed by hydrolysis, extraction and distillation. These processes have disadvantages, in that materials used in the processes are expensive, corrosive, difficult to prepare owing particularly to their sensitivity to moisture, and cumbersome to handle on a large scale.

SUMMARY OF THE INVENTION

In one aspect the present invention provides a process for preparing a mono or di-arylphosphine, which process comprises reacting an aryl compound bearing a leaving group attached to a carbon atom of the aromatic ring with phosphine in the presence of a Group VIII metal catalyst.

In accordance with the invention it is possible to avoid or alleviate many of the abovementioned disadvantages by reacting phosphine with an aryl compound in the presence of, preferably, a palladium catalyst.

A particular advantage of the present invention is that it is possible to obtain mono-arylphosphines and di-arylphosphines, i.e., primary and secondary arylphosphines, in good yield, and accompanied by only relatively small amounts of triaryl, i.e., tertiary phosphine. Owing to the high reactivity of phosphorus compounds, reactions to form arylphosphines usually proceed quickly to the triaryl compound. Consequently, triarylphosphines are available much more readily and cheaply than the corresponding mono- and di-arylphosphines. The mono- and di-arylphosphines are of considerable interest, particularly as intermediates and also as components of catalyst for many reactions. Their possibilities have not been exploited, however, owing to their relative inaccessibility and high price. By means of the present invention, and by careful selection of reaction conditions such as temperature and pressure, it is possible to influence the relative amounts of mono-, di- and tri-arylphosphines produced.

The aryl compound can have only carbon atoms in the ring, or can be heterocyclic containing one or more nitrogen, oxygen or sulphur atoms. As nitrogen-containing compounds there are mentioned, e.g. pyridine, pyrimidine, piperazine, pyrazole. As an oxygen-containing heterocyclic compound there is mentioned furan. As a sulphur-containing heterocyclic compound there is mentioned thiophene. Examples of hydrocarbyl aryl compounds include phenyl, α-naphthyl, β-naphthyl, biphenyl, phenanthrenyl, anthracenyl, naphthacenyl and 2,2'-bis(1,1'-binaphthyl) groups.

Preferred leaving groups are the halogens, particularly chlorine, bromine and iodine. Other suitable leaving groups include, for example, trifluoromethane-sulfonyloxy, methanesulfonyloxy, toluenesulfonyloxy and trifluoroacetate groups. The leaving group is attached to a carbon atom of the aryl ring. The aryl compound can bear one or more than one leaving group. Examples of aryl groups that bear two leaving groups, and therefore may bear two phosphorus atoms after reaction, include the 1,2-phenyl group, the 1,4-phenyl group, the 2,2'-biphenyl group of formula

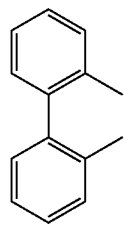

and the 2,2'-bis(1,1'-binaphthyl) group of formula

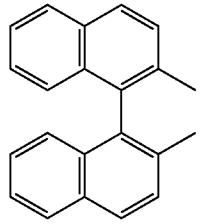

The aryl halide is preferably an iodo- or a bromo-compound. The aryl moiety can be unsubstituted or can be substituted by groups that do not interfere with the reaction. Such substituents include hydrocarbyl groups such as alkyl, alkenyl and cycloalkyl groups. Mention is made of alkyl and alkenyl groups, straight chained or branched, having up to about 8 carbon atoms, cycloalkyl groups having from 3 to 8 carbon atoms and aryl groups such as phenyl or naphthyl, aralkyl groups such as benzyl or phenethyl and alkaryl groups such as tolyl or xylyl groups. Other substituents include acyl, acyloxy, alkoxy, alkenoxy and aryloxy groups, again having up to about 8 carbon atoms. Particular compounds include bromotoluenes, bromoxylenes, iodotoluenes and iodoxylenes. The preferred aryl halides are bromobenzene and, especially, iodobenzene.

As stated above, the aryl compound can bear substituents that do not participate in the reaction with phosphine. It is found that the reaction of the present invention goes better with electron-withdrawing groups, for instance trifluoromethyl, cyano, alkylcarbonyl and alkoxycarbonyl. The substituted compounds that are of greatest interest, however, are those that bear electron-donating groups, for instance lower alkyl and lower alkoxy groups. The aryl compound can bear one, two or more substituents. To avoid steric interference it is preferred that the substituents shall be in the 3-, 4- or 5-position, relative to the leaving group. Mention is made of 3-trifluoromethyl-phenyl, 4-trifluoromethylphenyl, 3-cyanophenyl, 4-cyanophenyl, 3-acetylphenyl, 4-acetylphenyl, 3-methoxycarbonylphenyl, 4-methoxycarbonylphenyl, 3-acetoxyphenyl, 4-acetoxyphenyl, 3-methylphenyl, 4-methylphenyl, 3,5-dimethylphenyl, 3-methoxyphenyl, 4-methoxyphenyl and 3,5-dimethoxyphenyl groups, and also aryl groups other than phenyl that are correspondingly substituted.

Phosphine is a gas under ambient conditions. The reaction with the aryl compound is preferably carried out under elevated temperature and pressure. The product of the reaction is a mixture of the mono-, di- and tri-aryl phosphines and the relative ratio of these three products varies, depending upon the temperature and pressure of the reaction, the amount of catalyst and the presence of a base as promoter. The particular reaction conditions selected will therefore depend upon the desired ratio of these products. Elevated temperature, decreased pressure, a greater amount of catalyst and a greater amount of base promoter all tend to increase the amount of the di-aryl product at the expense of the mono-. Temperatures from 70° C. to about 150° C. are suitable, preferably from about 90 to 120° C. The pressure may be in the range from ambient to about 600 psig.

The reaction is carried out in the presence of a catalyst that is a metal of Group VIII of the Periodic Table, or a compound of such a metal. Most suitable are the precious metals of Group VIII, of which palladium is preferred. Mention is made particularly of zero valence compounds of palladium examples of which include tetrakis(triphenylphosphine)palladium, 1,2 bis(diphenylphosphine)ethane palladium, dichlorobis(triphenylphosphine)palladium, 1,3-bis(diphenylphosphine)-propane palladium, 1,4-bis(diphenyl-phosphine)butane palladium and 1,1-bis(diphenylphosphine)-ferrocene palladium.

Mention is made particularly of adducts of a Pd(II) salt and a tertiary phosphine, especially 1:1 adducts as catalysts. As palladium salts there are mentioned the diacetate and the dichloride. The tertiary phosphine can be a trialkylphosphine, for instance, tri(ethyl)-, tri(propyl)-, tri(n-butyl)-, tri(isobutyl)-, tri(cyclopentyl)-, tri(cyclolhexyl)- and tri(n-octyl)phosphine or a triarylphosphine, of which triphenylphosphine and tri(ortho-tolyl)phosphine are preferred. One preferred catalyst is an adduct of palladium (II) acetate and tris(o-tolyl)phosphine and is described (in German) by Wolfgang A. Herrmann et al., in Angew. Chem., 1995, Volume 107, pages 1989–1992 and (in English translation) in Angew. Chem. Int. Ed. Engl., 1995, Volume 34, pages 1844–1848, the disclosure of which is incorporated by reference.

Mention is made also of palladium compounds that are standard $\pi$ donors, for instance $Pd[cyclooctadiene]_2$, $Pd[cyclopentadiene]_2$ and $Pd[dibenzylacetone]_2$.

The amount of catalyst can range from about 0.05 mole to about 10.0 mole percent, preferably from about 0.1 to about 7.5 mole percent of the aryl compound initially charged.

It is possible to form the catalyst and then add it to the reaction vessel, or it is possible to add the components of the catalyst, so that the catalyst is formed in situ.

The reaction is preferably carried out in the presence of a solvent. Suitable solvents include glyme, acetonitrile, diethyl ether, anisole, di-n-butyl ether, tetrahydrofuran, p-dioxane, toluene, xylene, cumene or a mixture of toluene and isopropanol (e.g. a 3:1 mixture). Also suitable are aliphatic, cycloaliphatic and aromatic hydrocarbons, including hexane, heptane, octane, cyclohexane, benzene and petroleum fractions boiling at 70–140° C. Solvents that have oxidising properties, such as DMSO, should be avoided. Toluene is most preferred.

As stated above the reaction is preferably carried out in the presence of a base promoter such as for example sodium hydroxide, potassium hydroxide, sodium carbonate, potassium carbonate, calcium carbonate, sodium bicarbonate, potassium carbonate, sodium ethoxide, potassium ethoxide, ammonium carbonate, ammonium bicarbonate, calcium oxide, calcium hydroxide, magnesium oxide, magnesium hydroxide or the like. Organic bases, particularly amines, can also be used. Mention is made of pyridine and pyridine derivatives and tertiary amines of which triethylamine, tributylamine, and other trialkylamines are preferred.

The phosphine is supplied to a closed reactor under pressure that is suitably in the range of from about 100 psig to 600 psig, preferably about 200 psig to about 500 psig. The temperature of the reactor is elevated to at least about 80° C. but does not usually exceed about 150° C. Preferably the temperature is in the range of from about 1000 to about 150° C. The reaction time may be up to about 6 hours, after which the reaction is quenched. Quenching is suitably carried out by cooling. The reactions between the aryl compound and phosphine do not proceed at reasonable rates much below about 90° C., so cooling the reaction mixture to below about 70 or 80° C. is effective. Shorter reaction time and less base both favour the production of mono-arylphosphine over di- and tri-arylphosphine, so these parameters can be varied in accordance with the desired product mixture.

The invention is further illustrated in the following examples.

EXAMPLE 1
Reaction of Iodobenzene with Phosphine at Low Pressure

A one liter toluene solution containing iodobenzene (250 g, 1.23 moles), triethylamine (150 g, 1.5 moles) and palladium dimer (1:1 adduct of palladium (II) acetate and tri(o-tolyl)phosphine, 1.2 g, 1.28 mmole, 0.1 mole %, based on numbers of moles of iodobenzene charged) was charged to a one gallon autoclave under a nitrogen blanket. The solution was maintained at 200 psig phosphine pressure and 100° C., with stirring at 500 rpm, for 5 hours. The autoclave mixture was then cooled to ambient temperature, vented and water (500 ml) was added to dissolve the triethylamine hydriodide salt formed during the reaction. The two liquid phases were discharged from the autoclave and the toluene phase was analysed by GC/FID. This phase was found to be composed of (relative proportions were determined by area percent integration), phenylphosphine (13%), diphenylphosphine (74%) and triphenylphosphine (3%) as well as unreacted iodobenzene (10%) and triethylamine. The total conversion of iodobenzene was approximately 90%. The identity of all of these arylphosphines was unambiguously established by both GC/MS and phosphorus NMR techniques, by comparison with spectra of authentic specimens of these materials.

Both phenylphosphine and diphenylphosphine were subsequently isolated in pure form by fractional distillation under vacuum.

EXAMPLE 2
Reaction of Iodobenzene with Phosphine at High Pressure

A one liter xylene solution containing iodobenzene (375 g, 1.84 moles), triethylamine (150 g, 1.5 moles) and the palladium dimer (1:1 adduct of palladium(II) acetate and tri(o-tolyl)phosphine, 1.20 g, 1.2 mmole, 0.07 mole %) was charged to a one gallon autoclave under a nitrogen blanket. The solution was maintained at 500 psig phosphine pressure and 110° C., with stirring at 500 rpm, for 5 hours. At this time the autoclave was cooled to ambient temperature, vented and discharged as described above. Analysis of the xylene phase by GC/FID (with area percent integration) gave only monophenylphosphine (9%) and diphenylphosphine (7%), with no sign of triphenyl-phosphine, for a total conversion of iodobenzene of approximately 16%.

Subsequently, the monophenylphosphine present in the mixture was completely converted to diphenylphosphine by maintaining this xylene solution at 100° C. for approximately 24 hours under a nitrogen blanket in the absence of phosphine. Final conversion of diphenylphosphine to the triphenyl-phosphine end product was observed to occur at a significantly faster rate once the monophenylphosphine had been substantially converted to diphenylphosphine.

EXAMPLE 3
Reaction of 3-Trifluoromethyliodobenzene with Phosphine

A one litre toluene solution containing 3-trifluoromethyliodobenzene (200 g, 0.73 mole), triethylamine (150 g, 1.5 moles) and palladium dimer (1:1 adduct of palladium (II) acetate and tri(o-tolyl)phosphine, 0.69 g, 0.73 mmoles, 0.1 mole %) was charged to a one gallon autoclave and maintained at 102° C. and 200 psig phosphine pressure for 5 hours as described above. A slight exotherm was observed during the first 30 min. of the experiment, which was controlled by means of internal cooling. After isolating it as described above, the organic phase was analysed by GC/FID and GC/MS and found to contain mono (3-trifluoromethylphenyl)phosphine (15%), bis(3-trifluoromethyl-phenyl)phosphine (59%) and tris(3-trifluoro-methylphenyl)-phosphine (5%) in addition to the unreacted 3-trifluoromethyl-iodobenzene (21%).

EXAMPLE 4
Reaction of 3,5-Dimethyliodobenzene with Phosphine

A one liter toluene solution containing 3,5-dimethyliodobenzene (161 g, 0.69 mole), triethylamine (150 g, 1.5 mole) and the palladium dimer (1:1 adduct of palladium (II) acetate and tri(o-tolyl)phosphine 1.75 g, 1.8 mmole, 0.27 mole %) was maintained at 105–110° C. and 200 psig phosphine pressure for 10 hours, then cooled, vented and discharged in the usual manner. Analysis of the toluene phase by GC/FID and GC/MS revealed the presence of mono (3,5-dimethylphenyl)-phosphine (14%) and bis(3, 5-dimethylphenyl)phosphine (12%) with the remainder being unreacted 3,5-dimethyliodobenzene (74%).

EXAMPLE 5
Reaction of 1,4-Diiodobenzene with Phosphine

A one liter xylene solution of 1,4-diiodobenzene (150 g, 0.50 mole), triethylamine (100 g, 1.0 mole) and the palladium dimer (1:1 adduct of palladium (II) acetate and tri(o-tolyl)phosphine 0.5 g, 0.5 mmole, 0.1 mole %) was maintained at 110° C. and 400 psig phosphine pressure for 6 hours, then cooled, vented and discharged in the usual manner. Analysis of the xylene phase by GC/FID and GC/MS revealed the presence of 4-iodophenylphosphine (17%), bis(4-iodophenyl)phosphine (5%) and 1,4-bis (phosphino)benzene (1%), with the remainder being unreacted 1,4-diiodobenzene.

Analogously, 1,2-bis(phosphino)benzene can be obtained from 1,2-diiodobenzene.

What is claimed is:

1. A process for preparing mono- and di-arylphosphines which comprises reacting an aryl compound having an aromatic ring, substituted with a leaving group attached to a carbon atom of the aromatic ring with phosphine in the presence of a Group VIII metal catalyst.

2. A process according to claim 1 wherein the catalyst is an adduct of a palladium (II) compound and a triaryl phosphine.

3. A process according to claim 2 wherein the catalyst is a 1:1 adduct of palladium (II) acetate and tri(ortho-tolyl) phosphine.

4. A process according to claim 1, 2 or 3 wherein the leaving group is a halogen.

5. A process according to claim 1 wherein the aryl compound substituted with the leaving group is iodobenzene.

6. A process according to claim 1 wherein the reaction is carried out at a temperature in the range from ambient temperature to about 120° C. and a pressure from ambient pressure to about 600 psig.

7. A process according to claim 1 wherein the reaction is carried out in the presence of toluene as solvent and triethylamine as base promoter.

* * * * *